United States Patent
Ji et al.

(10) Patent No.: US 8,952,201 B2
(45) Date of Patent: Feb. 10, 2015

(54) SEPARATION METHOD OF ACETOPHENONE AND A-METHYLBENZYL ALCOHOL

(71) Applicant: Sun Yat-Sen University, Huizhou (CN)

(72) Inventors: Hongbing Ji, Huizhou (CN); Kungang Chai, Huizhou (CN)

(73) Assignee: Sun Yat-Sen University (CN)

( * ) Notice: Subject to any disclaimer, the term of this patent is extended or adjusted under 35 U.S.C. 154(b) by 0 days.

(21) Appl. No.: 13/882,766

(22) PCT Filed: Dec. 27, 2012

(86) PCT No.: PCT/CN2012/087611
§ 371 (c)(1),
(2) Date: May 1, 2013

(87) PCT Pub. No.: WO2013/143339
PCT Pub. Date: Oct. 3, 2013

(65) Prior Publication Data
US 2015/0018580 A1    Jan. 15, 2015

(30) Foreign Application Priority Data
Mar. 26, 2012    (CN) .......................... 2012 1 0082077

(51) Int. Cl.
C07C 45/78    (2006.01)
C07C 45/86    (2006.01)
C07C 29/94    (2006.01)

(52) U.S. Cl.
CPC ................. *C07C 45/86* (2013.01); *C07C 29/94* (2013.01)
USPC .......................................... 568/324

(58) Field of Classification Search
USPC ....................................... 568/324
See application file for complete search history.

(56) References Cited

FOREIGN PATENT DOCUMENTS

CN    101891609 A    11/2010

OTHER PUBLICATIONS

International Search Report, PCT/CN2012/087611, Int'l File Date: Dec. 27, 2012; Sun Yat-Sen University.

*Primary Examiner* — Sikarl Witherspoon
(74) *Attorney, Agent, or Firm* — Schmeiser, Olsen & Watts, LLP

(57) ABSTRACT

A method of inclusive separation of acetophenone and α-methylbenzyl alcohol is provided. According to the different binding ability of Cyclodextrin (CDs) with acetophenone and α-methylbenzyl alcohol, selective separation in mild condition can be possible. This has the advantages of mild separation conditions, high separation efficiency, simplicity, reuse ability of separation media, energy conservation and environmental protection, etc.

7 Claims, 1 Drawing Sheet

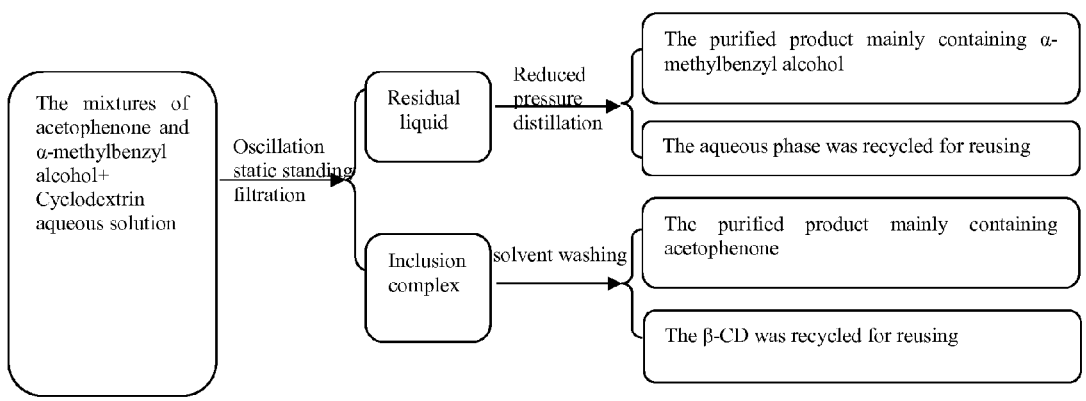

SEPARATION METHOD OF ACETOPHENONE AND A-METHYLBENZYL ALCOHOL

FIELD OF TECHNOLOGY

The following involves a separation method of the acetophenone and α-methylbenzyl alcohol.

BACKGROUND

Acetophenone and α-methylbenzyl alcohol are essential organic chemical materials. Acetophenone, which can be used as solvent, spice, plasticizer and chemical intermediate, is widely used in the field of soap, spice, medicine, etc. α-Methylbenzyl alcohol, which is also named as α-benzene ethanol or styracitol, can be used for mixing the chemical essence or as the raw material of the preparation of α-Methylbenzyl acetate and 1-phenylethyl propionate. There are large amounts of acetophenone and α-methylbenzyl alcohol in some raw materials, byproducts and wastes many petrochemical enterprises. The total content is more than 90% in all. However, some manufacturers don't dispose the mixed materials but sell them as low-value-added products directly. Therefore, the recycling of acetophenone, α-methylbenzyl alcohol products has significant economic and environmental benefits.

At present, the separation of acetophenone and α-methylbenzyl alcohol is generally resolved by rectification process. To achieve the optimization of the mass transfer process in distillation column, the distillation separation process is deeply investigated, such as the developing new packing. Yet because of the quite similar physical properties of acetophenone and α-methylbenzyl alcohol, for example, the diffidence of their melting and boiling points is only 1.6° C. under ordinary pressure. Therefore, acetophenone and α-methylbenzyl can be barely separated by ordinary distillation separation or crystallization methods, etc. It needs to increase the number of plates or to use the special rectification method to achieve a fine separation between them.

As the one of the most important host compounds in the supramolecular chemistry, cyclodextrin (CDs) and its derivatives are widely used in separation technology such as molecular imprinting, high performance liquid chromatography, capillary electrophoresis and membrane separation. In recent years, some studies on the host cyclodextrin about selective separation of organic compounds which have similar structures and melting or boiling points by the molecular recognition have been reported. Patent (CN 101891609A) discloses a method of selective separation of 4-bibenzoic acid and 3-bibenzoic acid with CDs as host molecules.

SUMMARY

One objective is to overcome the deficiencies of the existing technology and to provide an efficient separation method of acetophenone and α-methylbenzyl alcohol.

In order to achieve the aims, the present invention employs the technologies as following:

In this invention, CDs compounds act as inclusion host, according to the different inclusion ability of CDs with them. Acetophenone and α-methylbenzyl alcohol can be selectively separated in gentle condition. The following steps including:

(1) Adds the mixture of acetophenone and α-methylbenzyl alcohol into a saturated aqueous solution containing CDs. Then it oscillates in the water bath while the temperature is kept at a certain value. The complex precipitation is separated out at lower temperature or room temperature statically.

(2) The precipitate is isolated through filtration followed by elution with organic solvent, and CDs can be recycled.

In the above separation method, the molar ratio of mixture to host β-CDs varies from 1/1 to 8/1.

In the above separation method, the range of water bath temperature is 25~70° C.

In the above separation method, the range of the oscillation time is 1 h~8 h.

In the above separation method, the organic solvent for elution can be either ethyl acetate or ethanol.

The separation method of the present invention is particularly suitable for the separation of acetophenone and α-methylbenzyl alcohol in the petrochemical products.

The present invention employs the β-cyclodextrin to separate the mixture of acetophenone and α-methylbenzyl alcohol with 1:1 molar ratio with the separation factor higher than 20. The separation effect is due to the high selectivity inclusion of the β-cyclodextrin with acetophenone.

Compared with the existing technologies, the present invention has the following advantages:
1. The present invention employs a mild separation process, avoiding the problems of high energy consumption and low efficiency which caused by traditional distillation and crystallization process for acetophenone and α-methylbenzyl alcohol have the similar physical properties.
2. The separation process of the present invention is green and clean, using CDs as inclusion host, water as a dispersion medium, ethyl acetate or ethanol as the extraction solvent which are nontoxic and harmless.
3. CDs in the present invention can be recycled, and the reusability is quite stable.
4. The material in the present invention is cheap and readily available. The separation process is simple and mild, which is easy to realize commercial process.

BRIEF DESCRIPTION

FIG. 1 is the flow-process diagram of Example 1.

DETAILED DESCRIPTION

Combine the embodiments of the experiments and the comparisons to make a further illustration. However, the scope of the protection of this invention is not limited to these examples.

Example 1

1.14 g of β-CD was prepared into saturated aqueous solution keeping in the water bath whose temperature is 45° C. Then 2.00 mmol acetophenone and 2.00 mmol α-methylbenzyl alcohol were added to the saturated solution of β-CD oscillating for 6 h, keeping the inclusion reaction solution at 4° C. for 40 h. Then the inclusion complex was filtered and washed by ethyl acetate. In the inclusion complex, the contents of acetophenone and α-methylbenzyl alcohol were 0.80 mmol and 0.05 mmol respectively in which the purity of acetophenone is 93.14%. The separation factor is 22.72. The process is shown in FIG. 1.

Example 2

1.14 g of β-CD was prepared into saturated aqueous solution keeping in the water bath whose temperature is 30° C. Then the ethanol solution containing 2.00 mmol acetophenone and 2.00 mmol a-methyl benzyl alcohol was added to the saturated solution of β-CD oscillating for 6 h, keeping the inclusion reaction solution at 4° C. for 40 h. Then the inclusion complex was filtered and washed by ethanol. In the inclusion complex, the contents of acetophenone and α-methylbenzyl alcohol were 0.94 mmol and 0.05 mmol respectively in which the purity of acetophenone is 95.14%. The separation factor is 38.46.

Example 3

1.14 g β-CD was prepared into saturated aqueous solution keeping in the water bath whose temperature is 30° C. Then the ethanol solution containing 2.00 mmol acetophenone and 2.00 mmol α-methylbenzyl alcohol was added to the saturated solution of β-CD oscillating for 1 h, keeping the inclusion reaction solution at 4° C. for 40 h. Then the inclusion complex was filtered and washed by ethyl acetate. In the inclusion complex, the contents of acetophenone and α-methylbenzyl alcohol were 0.90 mmol and 0.04 mmol respectively in which the purity of acetophenone is 95.25%. The separation factor is 34.92.

Example 4

1.14 g β-CD was prepared into saturated aqueous solution keeping in the water bath whose temperature is 30° C. Then the ethanol solution containing 2.00 mmol acetophenone and 2.00 mmol α-methylbenzyl alcohol was added to the saturated solution of β-CD oscillating for 2 h, keeping the inclusion reaction solution at 4° C. for 12 h. Then the inclusion complex was filtered and washed by ethanol. In the inclusion complex, the contents of acetophenone and α-methylbenzyl alcohol were 0.96 mmol and 0.05 mmol respectively in which the purity of acetophenone is 95.01%. The separation factor is 36.63.

Example 5

1.14 g β-CD was prepared into saturated aqueous solution keeping in the water bath whose temperature is 30° C. Then 2.00 mmol acetophenone and 2.00 mmol α-methylbenzyl alcohol were added to the saturated solution of β-CD oscillating for 2 h, keeping the inclusion reaction solution at 4° C. for 24 h. Then the inclusion complex was filtered and washed by ethyl acetate. In the inclusion complex, the contents of acetophenone and α-methylbenzyl alcohol were 0.98 mmol and 0.05 mmol respectively in which the purity of acetophenone is 94.88%. The separation factor is 37.79.

Example 6

1.14 g β-CD was prepared into saturated aqueous solution keeping in the water bath whose temperature is 30° C. Then 1.00 mmol acetophenone and 4.00 mmol α-methylbenzyl alcohol were added to the saturated solution of β-CD oscillating for 2 h, keeping the inclusion reaction solution at 4° C. for 24 h. Then the inclusion complex was filtered and washed by ethyl acetate. In the inclusion complex, the contents of acetophenone and α-methylbenzyl alcohol were 0.41 mmol and 0.40 mmol respectively in which the purity of acetophenone is 50.18%. The separation factor is 6.47.

Example 7

1.14 g β-CD was prepared into saturated aqueous solution keeping in the water bath whose temperate is 30° C. Then 4.00 mmol acetophenone and 1.00 mmol α-methylbenzyl alcohol were added to the saturated solution of β-CD oscillating for 2 h, keeping the inclusion reaction solution at 4° C. for 24 h. Then The inclusion complex was filtered and washed by ethyl acetate. In the inclusion complex, the contents of acetophenone and α-methylbenzyl alcohol were 1.09 mmol and 0.01 mmol respectively in which the purity of acetophenone is 99.26%. The separation factor is 50.14.

Example 8

5.68 g β-CD was prepared into saturated aqueous solution keeping in the water bath whose temperature is 45° C. Then 1.20 g acetophenone and 1.22 g a-methyl benzyl alcohol were added to the saturated solution of β-CD oscillating for 2 h, keeping the inclusion reaction solution at 4° C. for 24 h. Then the inclusion complex was filtered and washed by ethyl acetate. In the inclusion complex, the contents of acetophenone and α-methylbenzyl alcohol was 0.67 g and 0.12 g respectively in which the purity of acetophenone is 85.23%. The separation factor is 12.74.

Example 9

5.68 g β-CD was prepared into saturated aqueous solution keeping in the water bath whose temperature is 45° C. Then 1.20 g acetophenone and 1.22 g a-methyl benzyl alcohol were added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 0.64 g and 0.08 g respectively in which the purity of acetophenone is 88.99%. The separation factor is 16.90.

Example 10

11.35 g β-CD was prepared into saturated aqueous solution keeping in the water bath whose temperature is 45° C. Then 2.42 g acetophenone and 2.44 g of α-methylbenzyl alcohol were added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 1.48 g and 0.26 g respectively in which the purity of acetophenone is 85.26%. The separation factor is 13.96.

Example 11

11.35 g β-CD was prepared into saturated aqueous solution keeping in the water bath whose temperature is 45° C. Then 1.92 g acetophenone and 0.50 g α-methylbenzyl alcohol were added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 1.01 g and 0.02 g respectively in which the purity of acetophenone is 97.64%. The separation factor is 22.06.

Example 12

5.68 g β-CD was prepared into saturated aqueous solution keeping in the water bath whose temperature is 45° C. 2.75 g petrochemical sample containing 36.52% acetophenone and 51.53% α-methylbenzyl alcohol was added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 1.67 g and 0.52 g respectively in which the purity of acetophenone is 86.66%. The separation factor is 13.29.

Example 13

5.68 g β-CD (recycled once) was prepared into saturated aqueous solution keeping in the water bath whose temperature is 45° C. Then 1.31 g acetophenone and 1.36 g α-methylbenzyl alcohol were added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 0.68 g and 0.11 g respectively in which the purity of acetophenone is 85.84%. The separation factor is 11.82.

Example 14

5.68 g β-CD (recycled twice) was prepared into saturated aqueous solution keeping in the water bath whose temperature is 45° C. Then 1.21 g acetophenone and 1.22 g α-methylbenzyl alcohol were added to the saturated solution of β-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 0.64 g and 0.10 g respectively in which the purity of acetophenone is 87.09%. The separation factor is 13.01.

Example 15

0.98 g α-CD was prepared into saturated aqueous solution keeping in the water bath whose temperature is 45° C. Then the mixture containing 0.49 g acetophenone and the same molar ratio of α-methylbenzyl alcohol was added to the saturated solution of α-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 0.03 g and 0.01 g respectively in which the purity of acetophenone is 68.42%. The separation factor is 2.10

Example 16

1.307 g γ-CD was prepared into saturated aqueous solution keeping in the water bath whose temperature is 45° C. Then the mixture containing 0.49 g acetophenone and the same molar ratio of α-methylbenzyl alcohol was added to the saturated solution of γ-CD oscillating for 2 h, keeping the inclusion reaction solution at room temperature for 24 h. Then the inclusion complex was filtered and washed by ethyl acetate. In the inclusion complex, the contents of acetophenone and α-methylbenzyl alcohol were 0.15 g and 0.04 g respectively in which the purity of acetophenone is 68.42%. The separation factor is 14.87.

What is claimed is:

1. A separation method of an acetophenone and α-methylbenzyl alcohol, wherein cyclodextrin (CDs) acts as an inclusion host and uses a different inclusion ability to separate the acetophenone and α-methylbenzyl alcohol.

2. The separation method of claim 1, further comprising:
    (a) adding a mixture of acetophenone and α-methylbenzyl alcohol into a saturated aqueous solution containing CDs oscillating in a water bath while the temperature is kept at a certain value, wherein a precipitate is separated out at a lower temperature or room temperature statically; and
    (b) isolating the precipitate through filtration followed by elution with an organic solvent, wherein the CDs are recycled.

3. The separation method of claim 1, wherein a molar ratio of mixture to host β-CD varies from 1/1 to 8/1.

4. The separation method of claim 2, wherein a range of water bath temperature is 25~70° C.

5. The separation method of claim 2, wherein a range of the oscillation time is 1 h~8 h.

6. The separation method of claim 2, wherein the organic solvent for elution is ethyl acetate or ethanol.

7. The separation method of claim 2, wherein the mixture of acetophenone and α-methylbenzyl alcohol is the by-product from petrochemical industry.

* * * * *